United States Patent [19]
Card

[11] Patent Number: 6,050,959
[45] Date of Patent: Apr. 18, 2000

[54] APPARATUS AND METHOD FOR MEASURING SEXUAL AROUSAL

[76] Inventor: Robert D. Card, 2227 E. Blaine Ave., Salt Lake City, Utah 84108

[21] Appl. No.: 09/079,309

[22] Filed: May 14, 1998

[51] Int. Cl.$^7$ ........................................................ A61B 5/00
[52] U.S. Cl. ............................................................... 600/587
[58] Field of Search ................................... 600/534–536, 600/587, 595

[56] References Cited

U.S. PATENT DOCUMENTS

| | | | |
|---|---|---|---|
| 4,469,108 | 9/1984 | Goldstein | 600/587 |
| 4,766,909 | 8/1988 | Timm et al. | 600/587 |
| 4,913,162 | 4/1990 | Leang et al. | 600/587 |
| 5,782,778 | 7/1998 | De Briere et al. | 600/587 |

*Primary Examiner*—Max Hindenburg
*Attorney, Agent, or Firm*—Mallinckrodt & Mallinckrodt

[57] ABSTRACT

An apparatus and method for sensing the swelling and shrinking of an elastic member based on movement and the angular changes to the surface of the elastic member between one or more portions of the surface thereof. The apparatus includes first and second parts which cooperate to produce an electrical signal indicative of the angular and distal positioning of the respective parts, with one of the parts preferably being a Hall effect device and the other a magnet. At least one part is mounted on a flexible base which attaches to a first portion of the surface of the elastic member for movement therewith with the other mounted for movement with a second surface portion of the elastic member. The apparatus and method are particularly adapted for use on a male penis and female breast for estimating sexual arousal based on the swelling of such body parts due to engorgement with blood which accompanies sexual arousal.

11 Claims, 7 Drawing Sheets

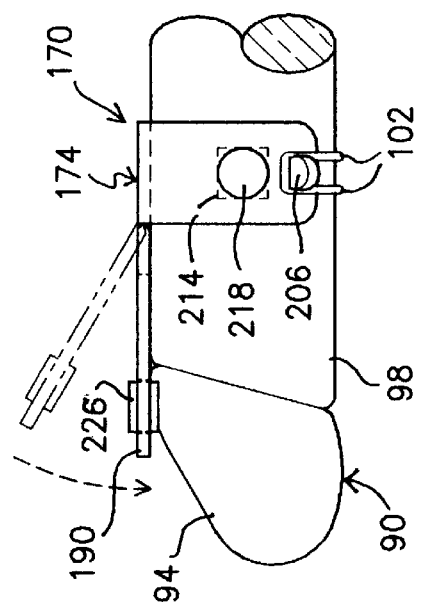
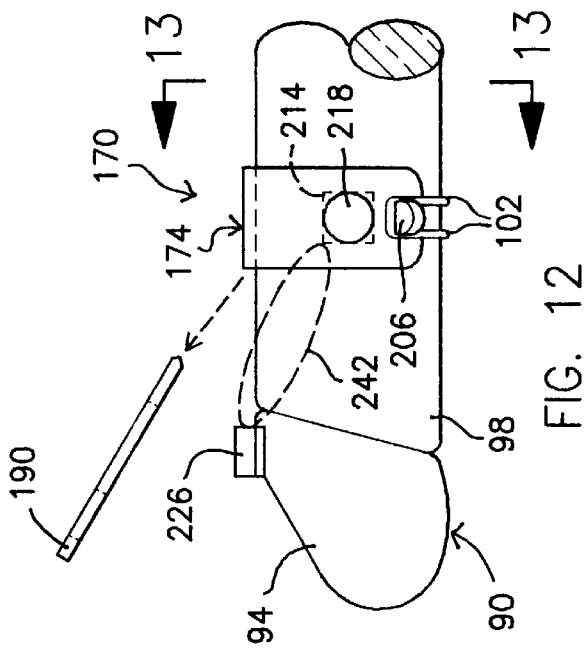
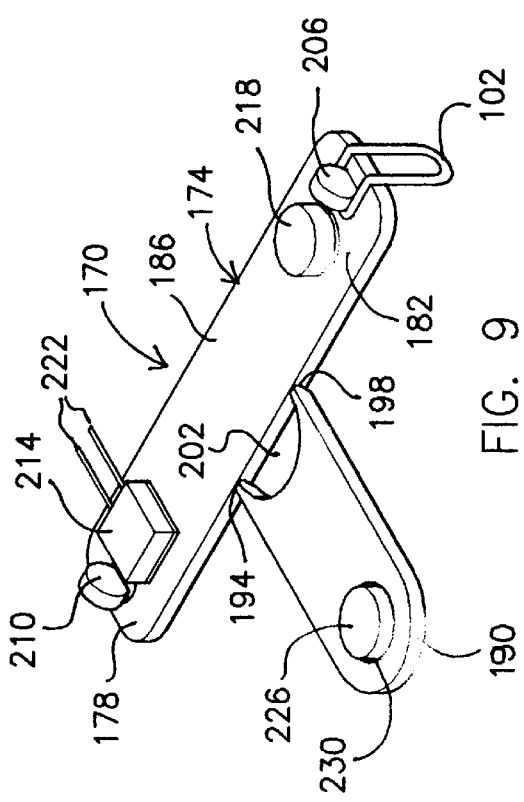
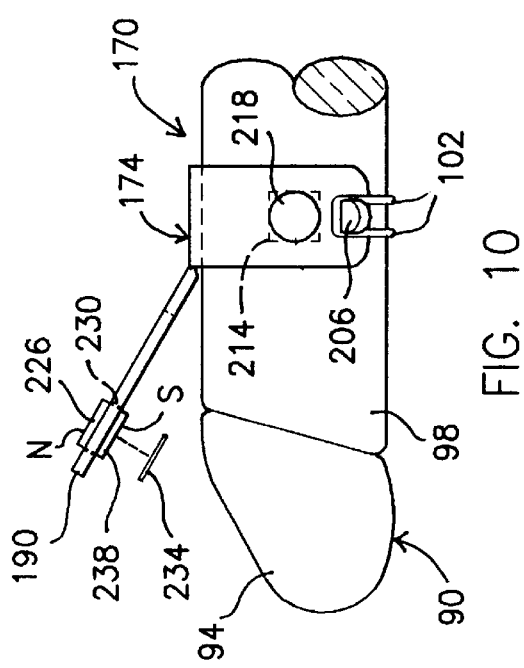

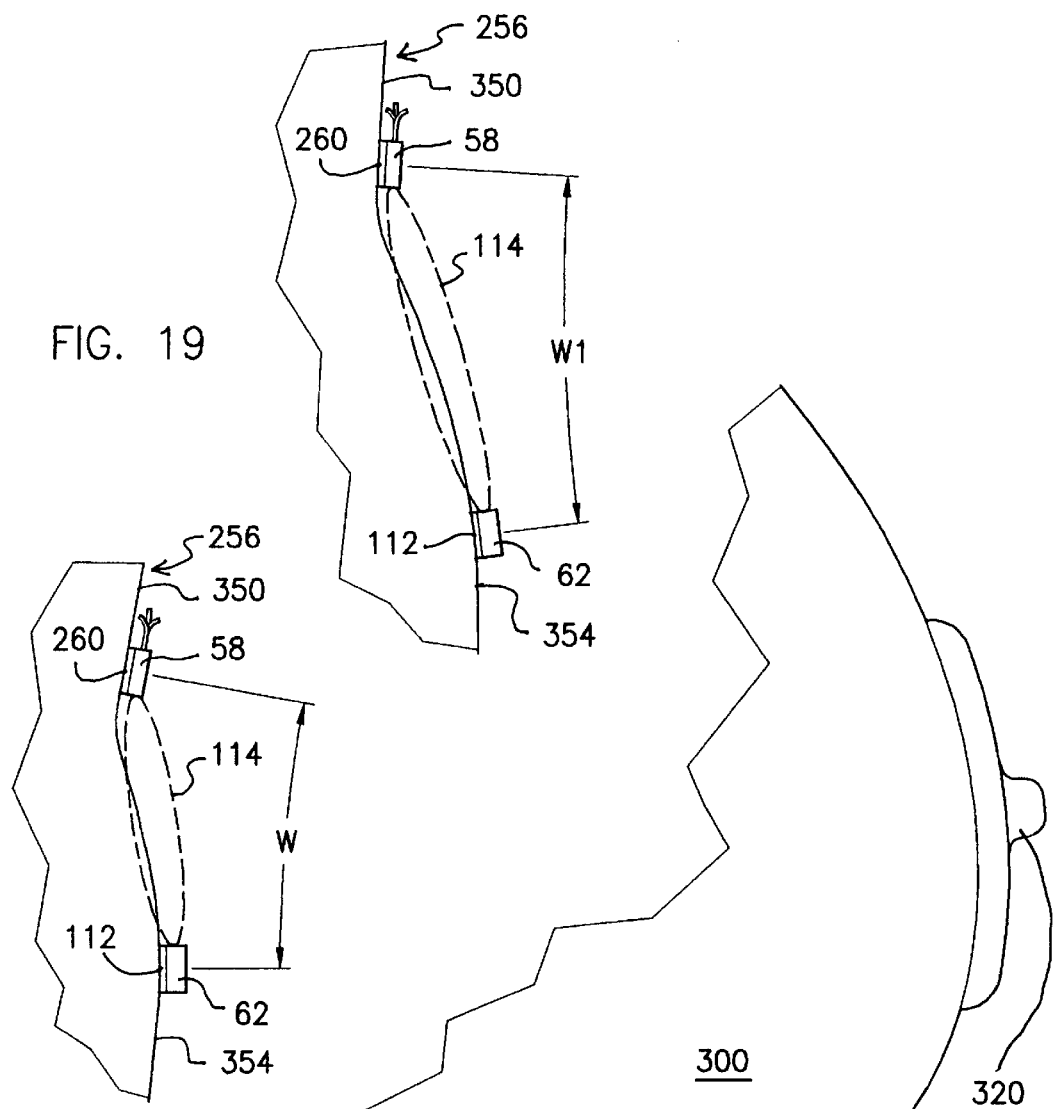
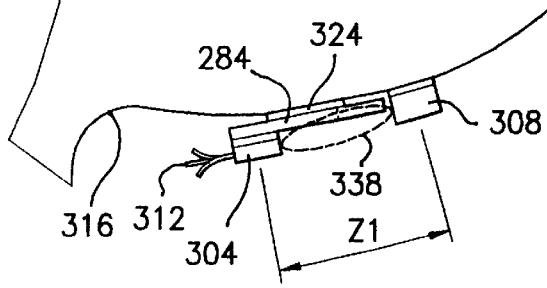
FIG. 19
FIG. 18
FIG. 17a

APPARATUS AND METHOD FOR MEASURING SEXUAL AROUSAL

BACKGROUND OF THE INVENTION

1. Field

The invention is in the field of devices and methods for sensing and measuring the swelling and shrinking of a flexible member using sensor devices particularly as related to sexual arousal in human beings.

2. State of the Art

The sensing and measurement of sexual arousal in human beings has been attempted over the years by means which detect the swelling and color changes of parts of the male and female human body due to engorgement with blood in response to sexual arousal. Observations include the change in color and swelling of the walls of the vagina, swelling of the breasts, and expansion due to blood flow, or tumescence of the penis. Such observations are particularly useful in diagnosing sexual dysfunctional problems, particularly in males, for assessing arousal patterns to various stimuli such as for determining deviant sexual tendencies in males for law enforcement and probational purposes, and for behavior modification.

The prior apparatus and methods of determining male sexual arousal are primarily based on the enlargement in diameter of the penis in response to sexual arousal. Such changes in diameter are primarily measured using three types of devices; a mercury-in-rubber detector, an indium gallium detector, and a flexible metal detector. However, each of the three devices are resistant to size changes and thus require a certain amount of force to deform, or stretch which can skew the actual measurements.

The mercury-in-rubber and the indium-gallium detectors measure the circumference of the penis and comprise a closed-ended, flexible tubing filled with mercury, and indium-gallium fluid, respectively, with an electrically conductive wire attached to opposite ends thereof and formed into a loop. The mercury and the indium-gallium fluid are both electrically conductive with the resistance thereof determined by the length and cross-sectional area of the liquid in the tube. The loop is sized to snugly fit around the shaft, or body of the a penis while in a non-aroused, or flaccid state. As the penis enlarges in diameter during sexual arousal, the flexible tubing is stretched, with the inner diameter thereof becoming smaller, such that the cross-sectional area of the mercury or the indium gallium therein becomes smaller, the length thereof becomes longer, and the electrical resistance of the fluid increases. By using an ohm meter connected to the respective wires of the device, the change in electrical resistance of the indium gallium can be measured as an indication of the increase in the diameter of the penis. Such devices must be of the correct size for the particular penis and are calibrated using a stepped conical gauge. They are only accurate when the penis is very hard and erect. Such devices are used once then must be disposed of.

The third device for sensing changes in the diameter of the penis is the flexible metal detector, which uses an arcuate, spring-steel band having one or more resistors, or strain gauges attached to the middle thereof. Size changes are measured by changes in resistance of the strain gauge using an ohm meter. Such device must be sized and calibrated for each particular size penis in the flaccid state and estimated erect state using a stepped, conical calibration gauge prior to each use. Such device is prone to tampering and being stretched out of calibration during use. They are expensive such that they are normally disinfected and reused.

Sensor devices such as those having two or more parts, such as Hall effect devices and the magnets used therewith are known in various arts for measuring distances. Hall effect devices operate by means of a constant current being applied through a plate therein and which plate produces a voltage potential crosswise thereto, which can be measured by means of a volt meter, when a magnetic field is applied perpendicularly thereto. The stronger the magnetic field, or flux, and the more perpendicular such flux lines are to the plate, the higher the crosswise voltage. Thus, when the first part, or Hall effect device is mounted to a member and the second part, or magnet is mounted to a second member which moves relative to the first member, the relative angular displacement and/or distance therebetween can be estimated based on the Hall effect voltage produced by the Hall effect device. Such devices have been used extensively on machinery and on a more limited basis on the human body such as to monitor the cervical dilation of expectant mothers and for use in joint and muscle rehabilitation.

Devices to sense the frequency of respiration comprising elastic belts which fit around the chest and which have indium-gallium or mercury switches to indicate respiration rate are widely known. These devices, however, do not indicate the depth of respiration. Recently, a respiration belt which utilizes a rather complex Hall effect type device has been developed which also measures respiration rate.

The use of galvanic skin response methods has been used for lie detection for many years. It comprises measuring the electrical resistance of the skin at the surface thereof, which varies depending on the amount of perspiration thereon. When a person lies, the conductivity of the skin generally increases with a corresponding decrease in electrical resistance is resistance is measured using a very sensitive ohm meter type device.

SUMMARY OF THE INVENTION

In accordance with the invention, an apparatus for attachment to a member the size of which increases and decreases based on fluid and/or gas content therein, preferably which is at least somewhat elastic, to sense the swelling and shrinking of such member based on the angularity and displacement of at least first and second surface portions of the elastic member. The apparatus includes sensor means having at least first and second parts which combine to produce an output signal based on the angularity and the relative displace of such parts from each other. The apparatus includes a flexible saddle, or base to which the sensor first part is attached and to which the second part may or may not be attached, which base serves to establish a fixed alignment and starting distance between the respective sensor first and second parts. The base is substantially non-stretchable but flexible and provides stable platform for the sensor first part which base rides over skin folds and which maintains the sensor first part in its initial alignment. The base is substantially flexible, though that is primarily dependent on the degree of curvature of the flexible member to which it must conform, and the base is substantially non-stretchable such that the initial distances and alignments are consistent. A primary function of the base is to compensate for differences in size of the flexible member, particularly when the flexible members are a penis. A second primary function of the base is to align and sets the distances between the respective sensor, then allows the sensor parts to move freely with the respective surfaces of the flexible member with which they are juxtaposed. While the sensor parts in any of the embodiments of the invention apparatus and methods may be of any conventional type, such as infrared or acoustic, the use of conventional Hall effect devices as sensor first parts and of permanent magnets as sensor second and third parts is preferred, though electromagnets can also be used with the Hall effect devices.

In a first embodiment of the apparatus of the invention designed primarily for use on a penis, and the associated method of use thereof, the base includes a first portion to which the sensor first part is attached and a second portion to which the sensor second part is removably connected. The base first portion attaches to the body of the penis and rides over the folds of a juxtaposed surface portion of the penis by means of a thin elastic band, which does not significantly constrict the penis for accurate measurements which are not significantly skewed. The second sensor part is removably attached, preferably to the head of the penis, such as by an adhesive or double-sided tape to move with a juxtaposed surface portion of the penis. The base second portion pivots away from the sensor second part and may be removed therefrom so as to allow the sensor second part to move freely. The sensor parts measure increases and decreases in penis length in response to sexual arousal.

In a second embodiment of the apparatus of the invention designed primarily for use on the penis, and the associated method of use thereof, the first and second sensor parts are affixed to first and second portions of an elongate base which wraps partially around the penis and is secured by a thin elastic band, which does not significantly constrict the penis for accurate measurements which are not significantly skewed. The sensor first and second parts are positioned at opposite sides of the penis such that they move with juxtaposed surface portions of the penis. The sensor parts measure increases and decreases in penis width in response to sexual arousal.

In a third embodiment of the apparatus of the invention designed primarily for use on the penis, and the associated method of use thereof, the first and second sensor parts are affixed to first and second portions of an elongate base which wraps partially around the penis and is secured by a thin elastic band, which does not significantly constrict the penis for accurate measurements which are not significantly skewed. The sensor first and second parts are positioned at opposite sides of the penis such that they move with juxtaposed surface portions of the penis. The base includes a third portion to which a sensor third part is removably attached, preferably to the head of the penis, such as by an adhesive or double-sided tape to move with a third surface portion thereof. The base third portion pivots away from the sensor second part and may be removed therefrom so as to allow the sensor second part to move freely. The apparatus senses the combined increase and decrease in penis length and width in response to sexual arousal.

A method of measuring the axial rigidity of a penis using sensor first and second parts includes removably mounting a sensor first part on the penis body for movement with the juxtaposed surface of the penis by means such as an adhesive or preferably double-sided adhesive tape adjacent to a person's body. A sensor second part is removably mounted to the penis body away from the person's body for movement with the juxtaposed surface of the penis by means such as an adhesive patch or preferably double-sided adhesive tape. When the penis is in a semi-erect state such that it is elongated to nearly its full erect length, the sensor first and second parts produce a signal which indicates the relative angle of the penis in response to sexual arousal. The penis can be deflected downwardly and released to measure deflection under a particular force and the rebound therefrom.

A method for monitoring the respiration rate and depth of breathing using sensor first and second parts includes removably mounting sensor first part in the region of a person's sternum for movement with the juxtaposed surface thereof, the sternum which acts as a fixed base therefore, by means such as an adhesive or preferably double-sided adhesive tape. The sensor second part is mounted in the region of the person's solar plexus, which moves with respiration, for movement with the juxtaposed surface thereof, by means of an adhesive or preferably double-sided adhesive tape. As the person breaths the sensor first and second parts produce a signal which indicates the frequency and the depth of such respiration, such as in response to sexual arousal.

In a fourth embodiment of the apparatus of the invention designed primarily for use on a female person's breast, and the associated method of use thereof, the base includes a first portion to which the sensor first part is attached and a second portion to which the sensor second part is removably connected. The base first portion attaches to the breast by means such as an adhesive or preferably double-sided tape for movement with the juxtaposed surface of the breast. The second sensor part is removably attached to the breast such as by an adhesive or preferably double-sided tape to move with a juxtaposed surface portion of the breast. The sensor parts measure increases and decreases in breast surface length in response to sexual arousal.

The embodiments of the apparatus of the invention and the methods can be used in various combinations which aid in the detection and measurement of sexual arousal in response to various audio and visual stimuli. This is primarily useful for law enforcement and penal use in assessing whether a person is a threat to children or society in general wherein the subject might wish to conceal sexual arousal to particular stimuli. A "Multiple Trace" method for male subjects includes simultaneous measurement of the penis as disclosed herein, galvanic skin response which is well known in the lie detection field, and respiration as disclosed herein. This combination makes concealment of sexual arousal difficult since a subject may be able to "fake" a response or non-response to one of the tests, it is difficult to "fake" all three.

THE DRAWINGS

The best mode presently contemplated for carrying out the invention is illustrated in the accompanying drawings, in which:

FIG. 1 is a perspective view of a first embodiment of the invention for measuring length and angular changes of a penis by means of a Hall effect device and a magnet;

FIG. 2, a side elevational view of such first embodiment showing the first portion of the base secured to the penis with an elastic band, the second base portion pivoted upwardly, and removable backing paper on the magnet;

FIG. 3, a side elevational view of such first embodiment showing the second base portion pivoted downwardly after removal of the backing paper to position the magnet on the penis;

FIG. 4, a side elevational view of such first embodiment showing the second base portion removed after placement of the magnet on the penis, with the magnet "V" distance from the Hall effect device;

FIG. 4A, a side elevational view corresponding to FIG. 4, showing the penis lengthened in response to sexual arousal with the magnet "V1" distance from the Hall effect device;

FIG. 5, a lateral vertical sectional view taken on the line 5—5 of FIG. 4 showing the elastic band attachment to ears of the first base portion;

FIG. 6, a perspective view of a second embodiment of the invention for measuring width changes of a penis by means of a Hall device and a magnet;

FIG. 7, a side elevational view of such second embodiment showing the magnet and second portion of the base secured to the penis with an elastic band;

FIG. 8, a lateral vertical sectional view taken on the line 8—8 of FIG. 7 showing the elastic band attachment to ears of the first and second base portions, with the magnet "X" distance from the Hall effect device;

FIG. 8A, a side elevational view corresponding to FIG. 8, showing the penis widened in response to sexual arousal with the magnet "X1" distance from the Hall effect device;

FIG. 9, a perspective view of a third embodiment of the invention having a third base portion with a second magnet extending from between the first and second base portions, for measuring length and width changes of a penis by means of a Hall effect device and the two magnets;

FIG. 10, a side elevational view of such third embodiment showing the magnet and second portion of the base secured to the penis with an elastic band, the third base portion pivoted upwardly, and removable backing paper on the second magnet;

FIG. 11, a side elevational view of such third embodiment showing the third base portion pivoted downwardly after removal of the backing paper to position the second magnet on the penis;

FIG. 12, a side elevational view of such third embodiment showing the third base portion removed after placement of the second magnet on the penis, with the second magnet "Y" distance from the Hall effect device;

FIG. 12A, a side elevational view corresponding to FIG. 12, showing the penis lengthened in response to sexual arousal with the second magnet "Y1" distance from the Hall effect device;

FIG. 13, a lateral vertical sectional view taken on the line 13—13 of FIG. 12 showing the elastic band attachment to ears of the first and second base portions, with the first magnet "Y2" distance from the Hall effect device;

FIG. 13A, a side elevational view corresponding to FIG. 13, showing the penis widened in response to sexual arousal with the first magnet "Y3" distance from the Hall effect device;

FIG. 14, a schematic diagram showing how the Hall effect transducer and a magnet can be utilized to measure angular displacement of the penis;

FIG. 15, a perspective view of a fourth embodiment of the invention for measuring length and angular changes of a breast by means of a Hall effect device and a magnet;

FIG. 16, a sectional view taken on the line 16—16 of FIG. 15, showing the adhesive patches with backing paper on the base first portion and the magnet such as prior to application to a breast;

FIG. 17, a side elevational view of the removal of the backing paper, attachment of the fourth embodiment to a breast, with the magnet "Z" distance from the Hall effect device;

FIG. 17A, a side elevational view corresponding to FIG. 17, showing the breast enlarged in response to sexual arousal with the second magnet "Z1" distance from the Hall effect device;

FIG. 18, a fragmentary side elevational view showing how the Hall effect transducer and a magnet can be utilized to measure the depth and frequency of respiration, shown in the exhaled position;

FIG. 19, a fragmentary side elevational view corresponding to FIG. 18, showing the relative positions of the Hall effect device and the magnet showing the inhaled position.

DETAILED DESCRIPTION OF THE ILLUSTRATED EMBODIMENTS

Figure 1:
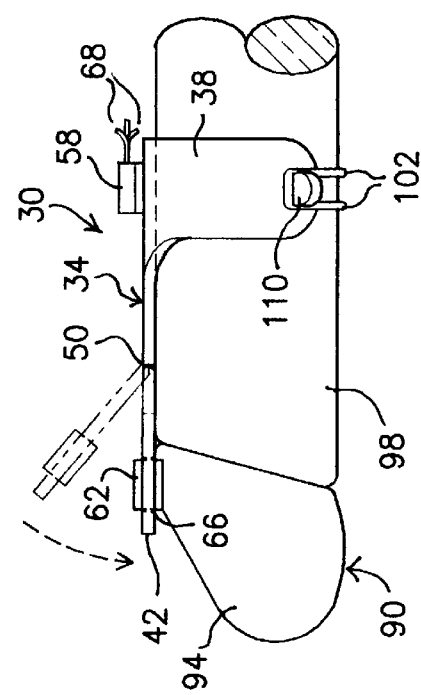
Figure 2:
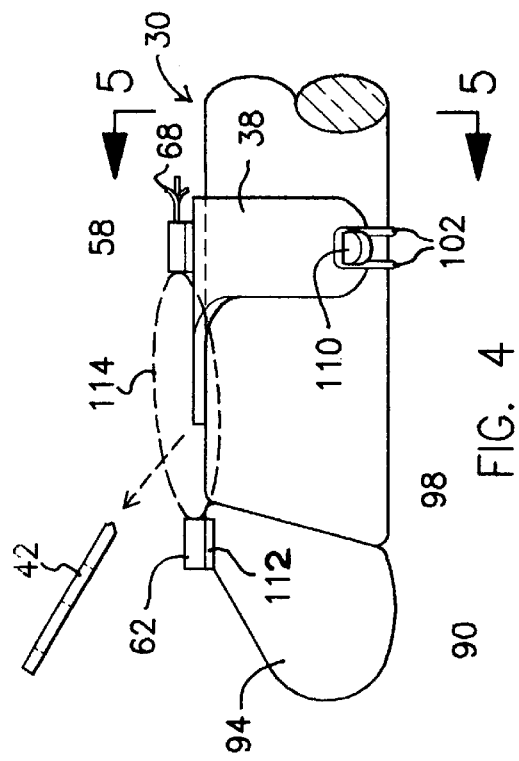
Figure 3:
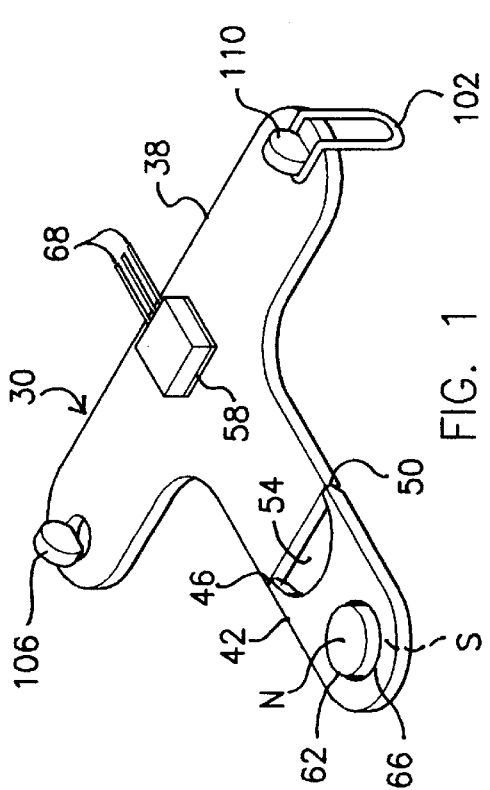

Referring to FIG. 1, therein is shown a first embodiment of the invention for use on a generally cylindrical, flexible member such as a man's penis. The apparatus 30 has a base 34 with a first portion 38 and a second portion 42 hingedly or removably attached to first base portion 38 by means of tabs 46 and 50, which remain after one or more perforations 54 are punched in base 34 between first base portion 38 and second base portion 42. Base 34 is substantially not stretchable, but is flexible such that it can be bent somewhat to more closely fit the general contour of a penis to which it is attached during use. The preferred material is plastic coated paper which is flexible but does not appreciably stretch, though most plastics alone will also work, such as being punched from sheet material or injection molded. The plastic coated paper preferably falls apart upon attempted disinfecting so as to prevent reusing thereof for sanitation purposes. A transducer first part 58, preferably a Hall effect device, is affixed to first base portion 38 with as an adhesive or double-sided adhesive tape. A transducer second part 62, preferably a permanent magnet made of neodymium, is removably positioned within an aperture 66 of second portion 42 for locating second part 62 relative to first part 58. Magnet 62 may be detachably connected to base second portion 42 within hole 66 by means such as being press-fit therein, an adhesive, or adhesive tape such as for transport prior to application. Three thin, flexible electrically conductive wires 68 extend from Hall effect device 58 from which an electrical current is produced in conjunction with transducer second part 62. Hall effect device 58 is oriented in the direction which produces the greatest electrical signal through wires 68 in an installed position on penis 90. Magnet 62 is oriented in the proper polarity, typically with the north or south pole facing upwardly and the other pole facing downwardly as shown in FIG. 1 though other orientations are possible, depending on the particular Hall effect device 58 so as to properly orient the magnetic field thereof relative to Hall effect device 58 to produce an appropriate electrical signal through wires 68, as is typical with such devices.

Apparatus 30 is used to measure elongation of a penis 90 in response to sexual arousal, which has a head 94 and body 98. First portion 38 of base 34 is removably attached to body 98 of penis 90 by means of a light elastic band 102 which is removably or permanently attached to base first portion 38 by means such as tabs 106 and 110 which are punched or molded in first portion 38. When tabs 106 and 110 are punched, they tend to spring back to the unpunched position so as to retain elastic band 102 attached thereto. After attachment to penis 90, base second portion 42 is pivoted upwardly about tabs 46 and 50 so as to expose a piece of backing paper 111 covering a double-sided adhesive tape or an adhesive patch 112 on magnet 62. After removal of backing paper 106, second portion 42 is pivoted downwardly such that adhesive patch 112 contacts head 94 of penis 90 so as to adhere thereto. Double-sided adhesive tape provides little resistance to expansion and contraction due to its flexible structure and is preferred for attachment of all first and second transducer parts. The pole which the adhesive or double-sided tape is applied to serves to assure that the magnet 62 is applied with the right polarity, which is also true for the other magnets. The penis head 94 is preferably where magnet 62 is placed as it is less wrinkled than penis body 98 in the flaccid state which enhances adhesion thereof. Thereafter, magnet 62 is pressed from hole 66 and second portion 42 is pivoted upwardly and may be removed from first portion 38 by breaking tabs 46 and 50. While the preferred position for magnet 62 is on head 94 of penis 90, it may also be positioned on body 98 thereof by moving base 34 away from head 94.

Figure 4:
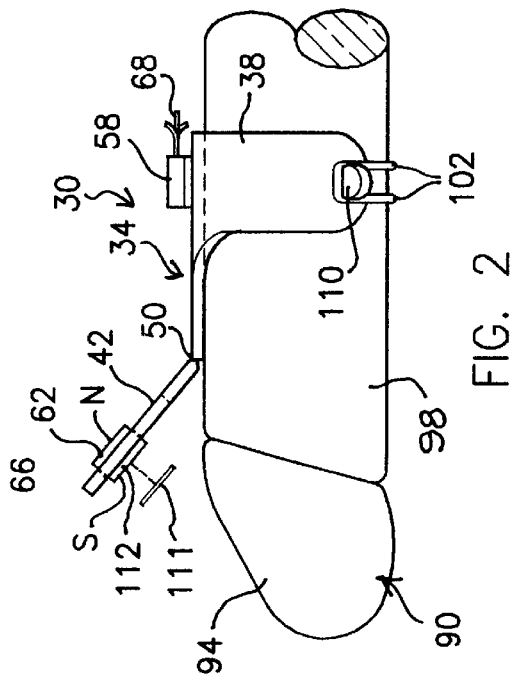
Figure 4A:
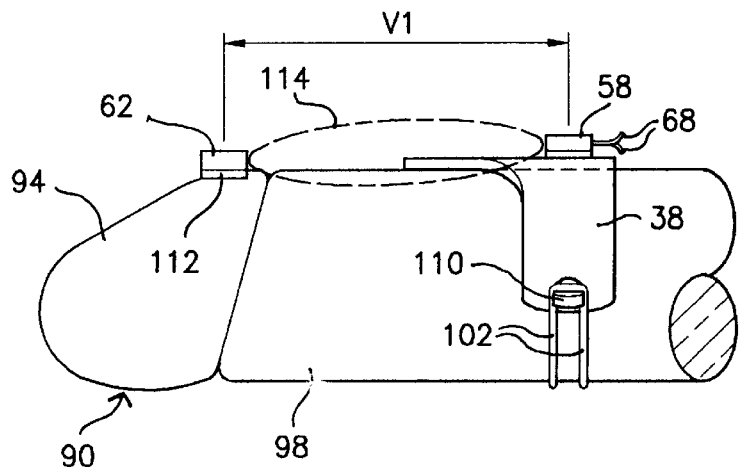

Referring to FIGS. 4 and 4A, in their initial positions following removal of base second portion 42, magnet 62 is at a distance "V" from Hall effect device 58. The magnetic field 114 of magnet 62 is of an initial strength at Hall effect device 58 based on the distance "V", the strength of field 114 produced by magnet 62, and the relative orientations of the poles of magnet 62 to Hall effect device 58. Hall effect device 58 produces an initial voltage output, or signal based on the strength of magnetic field 114 at Hall effect device 58 which signal can be monitored by conventional means such as a volt meter. As penis 98 engorges with blood during sexual arousal, head 94 and body 98 lengthen such that distance "V" increases to distance "V1". Magnetic field 114 is weaker at Hall effect device 58 at such increased distance such that a reduced output signal is carried through wires 68. Since the relative orientations of magnet 62 to Hall effect device 58 remain relatively unchanged, the change in the signal between unaroused distance "V" and aroused distance "V1" is an indicator of the change in distance due to engorgement of the penis with blood due to sexual arousal.

Figure 6:
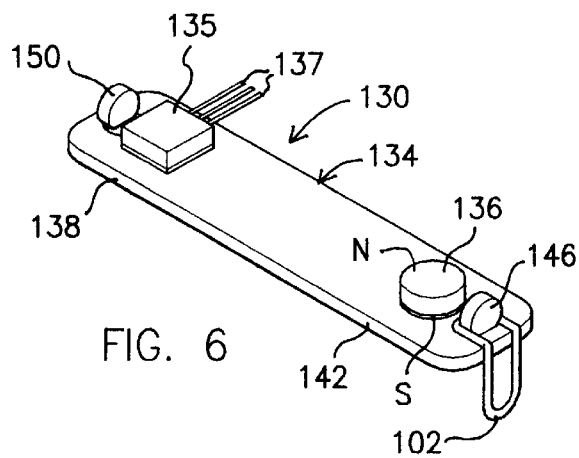
Figure 7:
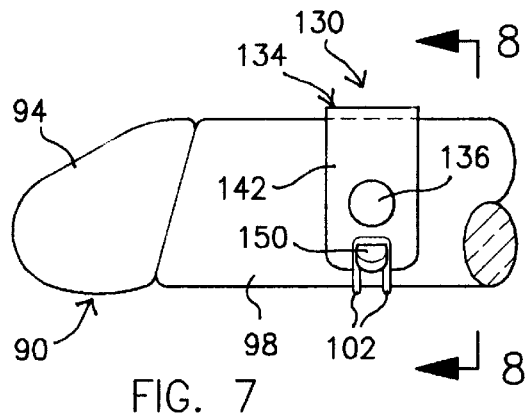

A second embodiment of the invention is shown in FIGS. 6 and 7, which apparatus 130 is used to measure the change in girth, or width of body 98 of penis 90 in response to sexual arousal. Apparatus 130 has a base 134 with a first portion 138 and a second portion 142. Base 134 is removably attached to body 98 of penis 90 by means of elastic band 102 which is removably or permanently attached to base first portion 138 and second portion 142 by means such as tabs 146 and 150, respectively, which are punched or molded as described previously. Base 134 is substantially not stretchable, but is flexible such that it can be bent around penis body 98 to closely fit the contour of penis 90 to which it is attached during use. The material and process is the same as for base 34 described previously. Transducer first and second parts 135 and 136 are affixed to body first and second portions 138 and 142, respectively, by means such as an adhesive or double-sided adhesive tape. The length of base 134 and/or the distance between sensor first and second parts 135 and 136 are varied based on the diameter or circumference of penis body 98 so as to be directly opposite each other when installed on penis body 98 in the flaccid state thereof. Three thin, flexible electrically conductive wires 137 extend from Hall effect device 135 from which an electrical current is produced in conjunction transducer second part 137. Hall effect device 135 is oriented in the direction which produces the greatest electrical signal through wires 137 in the installed position on penis 90. Second part 136, preferably a permanent magnet made of neodymium, is oriented in the proper polarity with the proper pole, north or south depending on the particular Hall effect device, typically facing upwardly and the other pole facing downwardly as shown in FIG. 6 though other orientations are possible, depending on the particular Hall effect device 135 so as to properly orient the magnetic field thereof relative to Hall effect device 135 to produce an appropriate electrical signal through wires 137, as is typical with such devices.

Figure 8A:
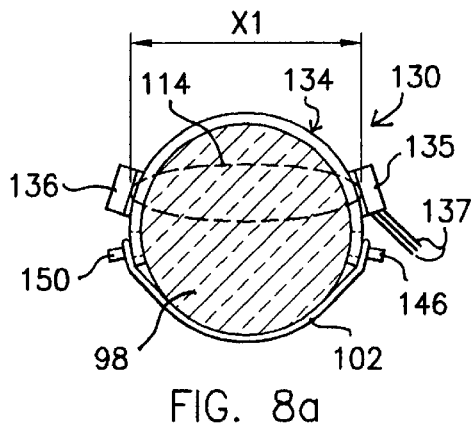
Figure 8:
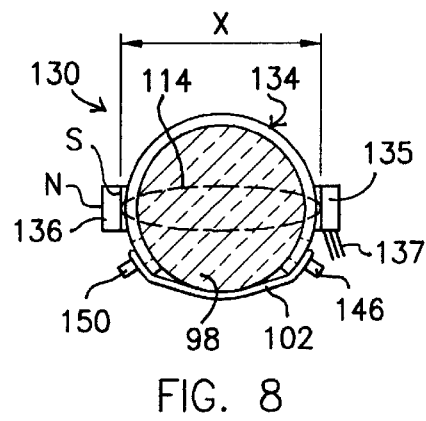

Referring to FIGS. 8 and 8A, in their initial positions magnet 136 is at a distance "X" from Hall effect device 135. The magnetic field 138 of magnet 136 is of an initial strength at Hall effect device 135 based on the distance "X", the strength of field 138 produced by magnet 136, and the relative orientations of the poles of magnet 136 to Hall effect device 135. As penis 98 engorges with blood during sexual arousal, body 98 widens such that distance "X" increases to distance "X1". Since the relative orientations of magnet 136 to Hall effect device 135 remain relatively unchanged, the change in the signal between unaroused distance "X" and aroused distance "X1" is an indicator of the change in distance due to engorgement of the penis with blood due to sexual arousal.

In FIG. 9 is shown a third embodiment of the invention which combines the first two embodiments into an apparatus 170 for making combined length and width measurements of penis 90 in response to sexual arousal output as a single signal. Apparatus 170 has a base 174 with a first portion 178, a second portion 182, a middle portion 186 therebetween, and a third portion 190 which is hingedly or removably attached to base middle portion 186 by means of tabs 194 and 198, which remain after one or more perforations 202 are punched in base 174 between base middle portion 186 and base third portion 190. Base 174 is removably attached to body 98 of penis 90 by means of elastic band 102 which is removably or permanently attached to base first portion 178 and second portion 182 by means such as tabs 206 and 210, respectively, which are punched or molded as described previously. Base 174 is substantially not stretchable, but is flexible such that it can be bent around penis body 98 to closely fit the contour of penis 90 to which it is attached during use. The material and process is the same as for base 34 described previously. Transducer first and second parts 214 and 218 are affixed to body first and second portions 178 and 182, respectively, by means such as an adhesive or double-sided adhesive tape. The length of base 174 and/or the distance between sensor first and second parts 214 and 218 are varied based on the diameter or circumference of penis body 98 so as to be directly opposite each other when installed on penis body 98 in the flaccid state thereof. Three thin, flexible electrically conductive wires 222 extend from Hall effect device 218 from which an electrical current is produced in conjunction transducer second part 218, preferably a permanent magnet made of neodymium. Hall effect device 214 is oriented in the direction which produces the greatest electrical signal through wires 218 in the installed position on penis 90. Magnet 218 is oriented in the proper polarity with the proper pole, north or south typically facing upwardly and the other facing downwardly as shown in FIG. 9 though other orientations are possible, depending on the particular Hall effect device so as to properly orient the magnetic field thereof relative to Hall effect device 214 to produce an appropriate electrical signal through wires 222, as is typical with such devices.

A transducer third part 226, preferably a permanent magnet made of neodymium and of smaller size than magnet 218 such that the magnetic field thereof is weaker, is removably positioned within an aperture 230 of base third portion 190 for locating third part 226 relative to first part 214. Magnet 226 is preferably weaker than magnet 218 since magnet 226 is typically closer in distance to Hall effect device 214 than is magnet 218 as installed on penis 90. Magnet 226 is oriented in the proper polarity with the proper pole, north or south typically facing upwardly and the other facing downwardly as shown in FIG. 9 though other orientations are possible, depending on the particular Hall effect device so as to properly orient the magnetic field thereof in the same general magnetic flux direction as that produced by magnet 218 relative to Hall effect device 214 so as to produce an electrical signal through wires 222 which is additive to that induced therein by magnet 218. This additive signal is an overall combined measurement of the lengthening and widening of penis 90. The magnetic field of magnet 226 can also be made to interfere with that of magnet 218 by reversing the polarity of magnet 218 or 226, which can be done to cancel out the effect of one or the other thereof if desired.

Magnet 226 attaches to penis head 94 similarly to magnet 62. After attachment of base 174 to penis 90, base third portion 190 is pivoted upwardly about tabs 194 and 198 so as to expose a piece of backing paper 234 covering an adhesive patch 238 magnet 226. After removal of backing paper 234, base third portion 190 is pivoted downwardly such that adhesive patch 238 contacts head 94 of penis 90 so as to adhere thereto. Thereafter, magnet 226 is pressed from hole 230 and base third portion 190 is pivoted upwardly and may be removed from base middle portion 186 by breaking tabs 194 and 198. While the preferred position for magnet 226 is on head 94 of penis 90, it may also be positioned on body 98 thereof by moving base 174 away from head 94.

Figure 12A:
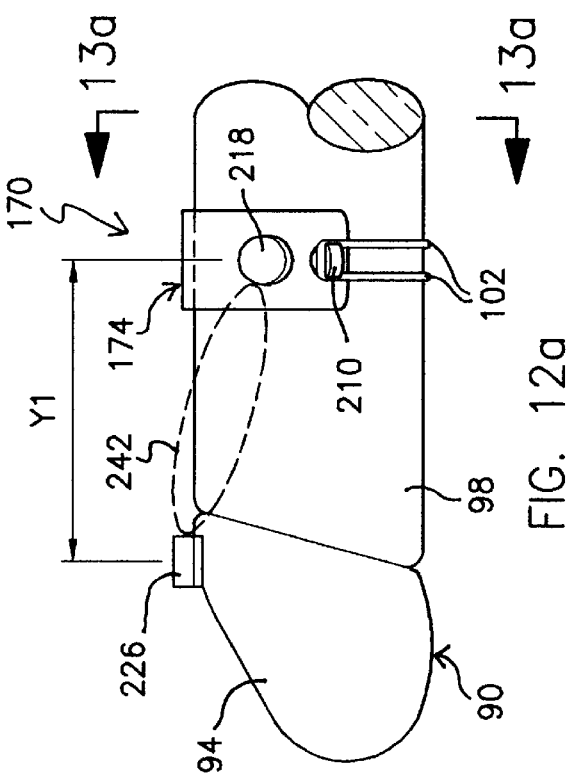

Referring to FIGS. 12 and 12A, in their initial positions following removal of base third portion 190, magnet 226 is at a distance "Y" from Hall effect device 214. The magnetic field 242 of magnet 226 is of an initial strength at Hall effect device 58 based on the distance "Y", the strength of field 242 produced by magnet 226, and the relative orientations of the poles of magnet 226 to Hall effect device 214. Hall effect device 214 produces an initial voltage output, or signal based partly on the strength of magnetic field 242 at Hall effect device 214 which signal can be monitored by conventional means such as a volt meter. As penis 98 engorges with blood during sexual arousal, head 94 and body 98 lengthen such that distance "Y" increases to distance "Y1". Magnetic field 224 is weaker at Hall effect device 214 at such increased distance such that a reduced output signal due to magnet 226 is carried through wires 222. Since the relative orientations of magnet 226 to Hall effect device 214 remain relatively unchanged, the change in the signal between unaroused distance "Y" and aroused distance "Y1" is an indicator of the change in length due to engorgement of the penis with blood due to sexual arousal.

Figure 13:
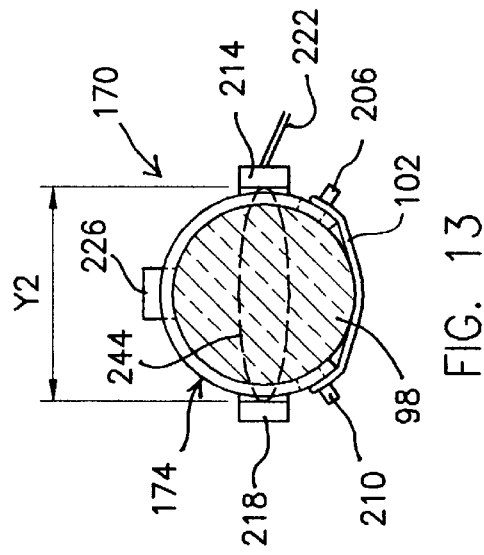
Figure 13A:
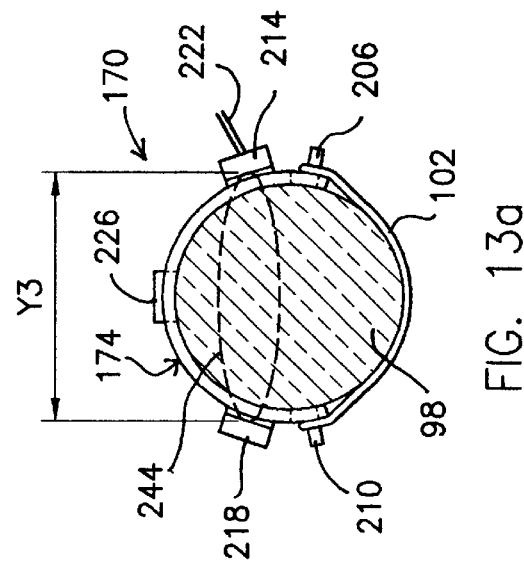
Figure 5:
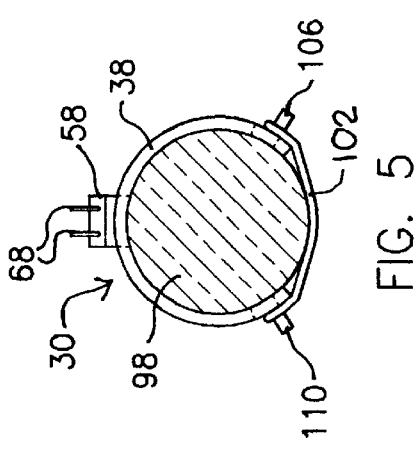

Referring to FIGS. 13 and 13A, in their initial positions magnet 218 is at a distance "Y2" from Hall effect device 214. The magnetic field 244 of magnet 218 is of an initial strength at Hall effect device 214 based on the distance "Y2", the strength of field 244 produced by magnet 218, and the relative orientations of the poles of magnet 218 to Hall effect device 214. As penis 98 engorges with blood during sexual arousal, body 98 widens such that distance "Y2" increases to distance "Y3". Since the relative orientations of magnet 218 to Hall effect device 214 remain relatively unchanged, the change in the signal between unaroused distance "Y2" and aroused distance "Y3" is an indicator of the change in distance due to engorgement of the penis with blood due to sexual arousal.

Figure 14:
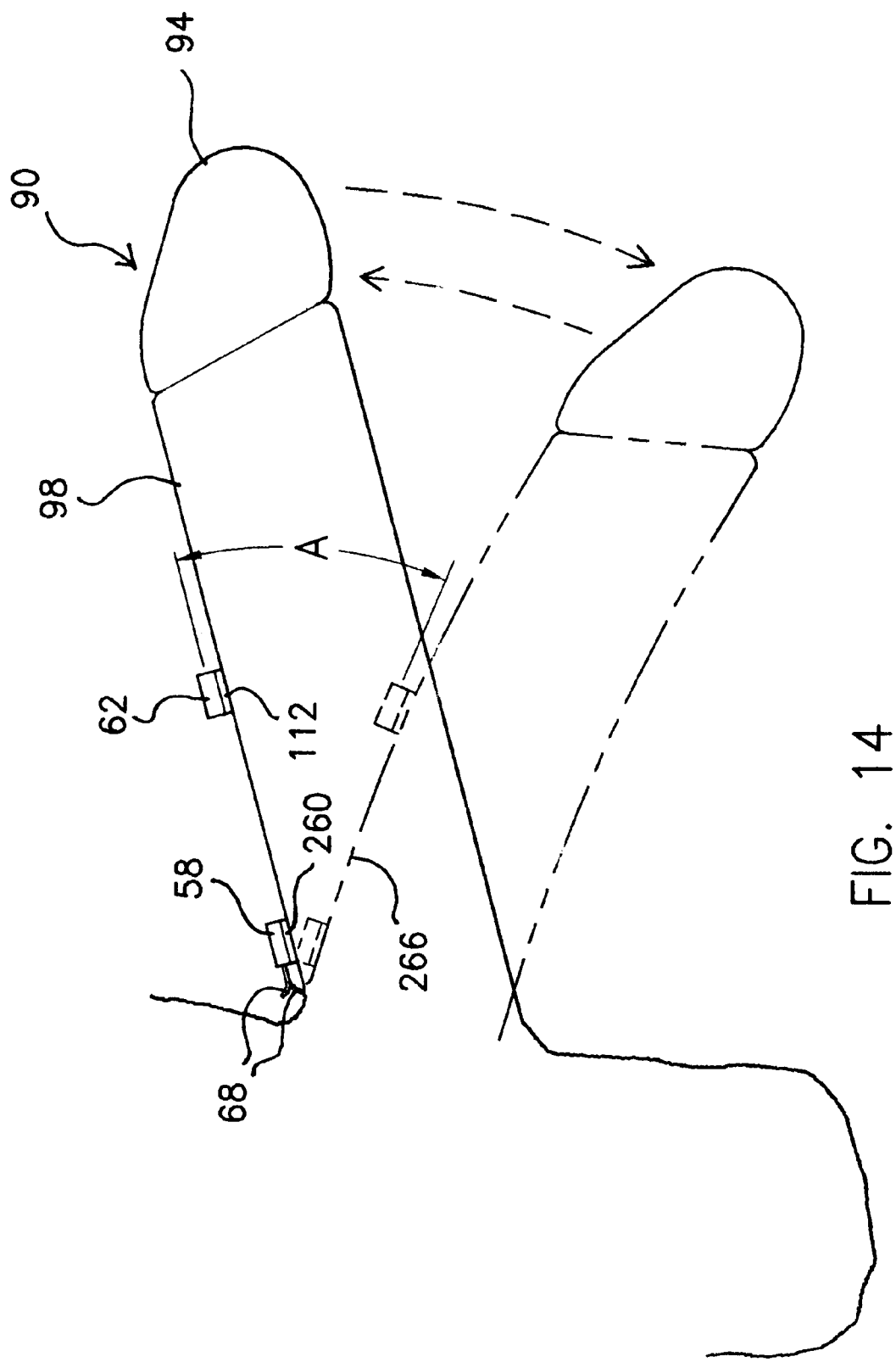

Referring to FIG. 14, therein is shown a method for measuring the axial rigidity of penis 90 under its own weight or by forcing the end thereof down and checking the time to rebound and the degree of rebound thereof using sensor first and second parts 58 and 62. A sensor first part, preferably a Hall effect transducer 58 is mounted on body 98 of penis 90 adjacent the attachment of the penis 90 by means of an adhesive patch or double-sided adhesive tape 260 adjacent to a person's body 256. A sensor second part, preferably a magnet 62 is mounted to body 98 of penis 90 away from body 256 by means of adhesive patch or double-sided adhesive tape 112 with the north or south pole facing upwardly and the other pole facing downwardly, depending on the particular Hall effect device 58. In the semi-erect position, shown in dotted lines, penis 98 is not flaccid but is not fully erect, such that body 98 is elongated but not straight and in fact droops such that there is a small angle "A" between Hall effect device 58 and magnet 62 since the portion of penis body 98 adjacent body 256 is held more in a horizontal orientation than the head 94 thereof. In such alignment, magnetic field 114 produces a first voltage, or signal in wires 68. As the penis 90 becomes erect due to sexual arousal, penis 90 moves to condition, shown in solid lines, wherein there is little additional lengthening of penis 90, but magnet 62 becomes approximately aligned with Hall effect device 58 such that magnetic field 114 thereof produces a second signal in wires 68 of Hall effect device 58 indicative of the angle "B" through which the penis has moved. This is angular measurement is particularly useful for measuring sexual arousal between sexually aroused states.

Figure 15:
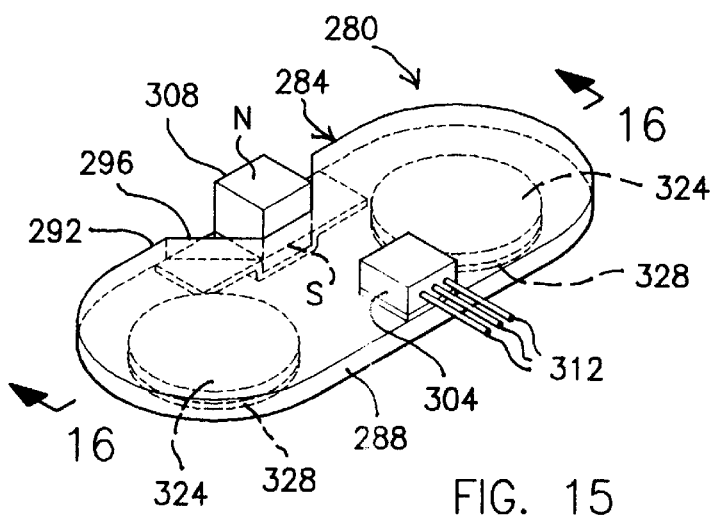
Figure 16:
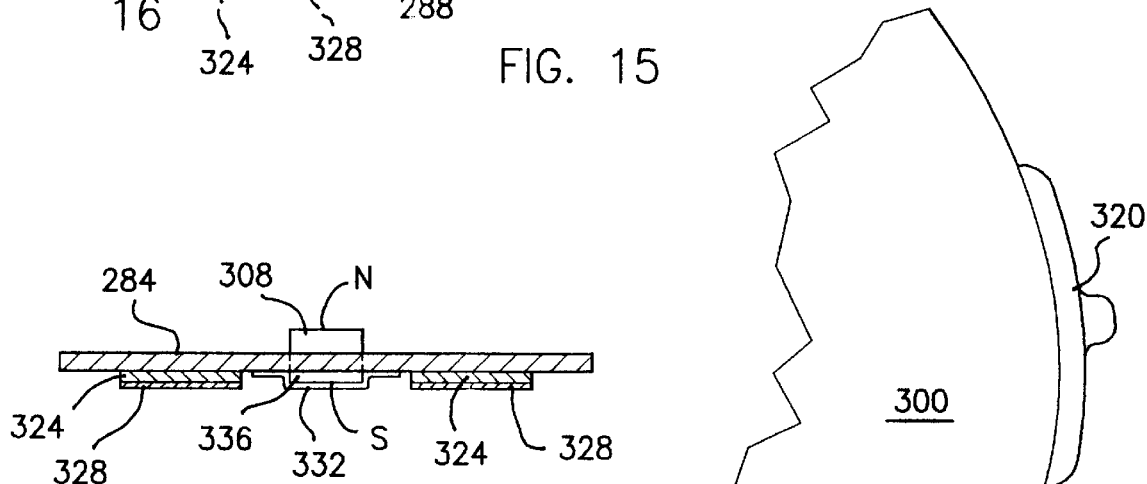

In FIG. 15 is shown a fourth embodiment of the invention which is specially adapted for application to less curved flexible members such as a woman's breast. The apparatus 280 has a base 284 with a rear, or first portion 288 and a front, or second portion 292 having a notch 296 therein. Base 284 is substantially not stretchable, but is flexible such that it can be bent to closely fit the contour of a breast 300 to which it is attached during use. The material and process is the same as for base 34 described previously. A transducer first part 304, preferably a Hall effect device, is affixed to base first portion 288 such as an adhesive or double-sided adhesive tape. A transducer second part 308, preferably a permanent magnet made of neodymium, is removably positioned within notch 296 of second portion 292 for locating second part 308 relative to first part 304. Magnet 308 may be detachably connected to base second portion 292 within notch 296 by means such as an adhesive or adhesive tape such as for transport prior to application. Three thin, flexible electrically conductive wires 312 extend from Hall effect device 58 from which an electrical current is produced in conjunction with transducer second part 62. Hall effect device 304 is oriented in the direction which produces the greatest electrical signal through wires 312 in an installed position on breast 300. Likewise, magnet 308 is oriented in the proper polarity with the proper pole, north or south typically facing upwardly and the other pole facing downwardly as shown in FIG. 15 though other orientations are possible, depending on the particular Hall effect device, so as to properly orient the magnetic field thereof relative to Hall effect device 58 so as to produce an appropriate electrical signal through wires 312, as is typical with such devices.

Apparatus 280 is used to measure enlargement of breast 300 by measuring the increase in outer surface length thereof in response to sexual arousal. First portion 288 of base 284 is removably attached to breast 300, preferably at a lower portion 316 of breast 300 away from nipple 320 thereof by means of a pair of adhesive pads 324 after removing backing paper 328 therefrom. After attachment of base 284 to breast 300, a piece of backing paper 332 covering an adhesive patch 336 on magnet 308 is removed and pressed against lower portion 316 of breast 300 to adhere thereto and to break free of base second portion 292. Notch 296 functions to initially position magnet 308 relative to Hall effect device 304.

Figure 17:
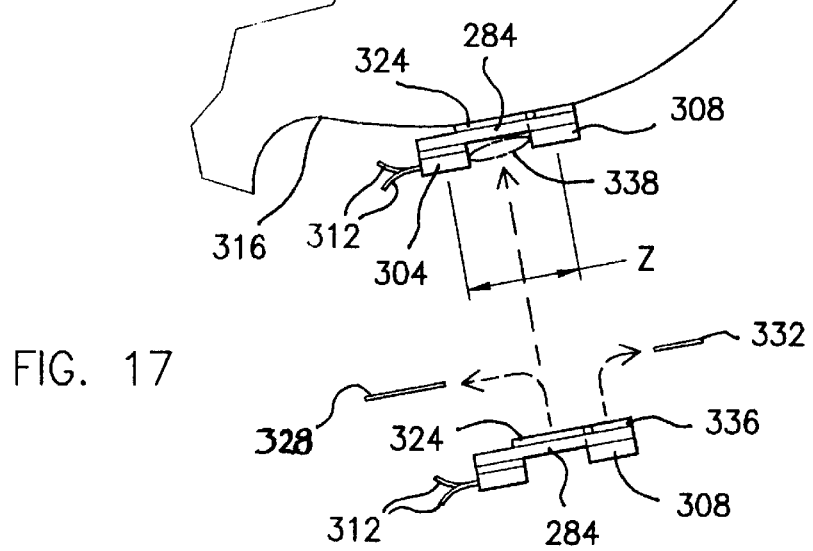

Referring to FIGS. 17 and 17A, in their initial positions magnet 308 is at a distance "Z" from Hall effect device 304.

The magnetic field 338 of magnet 308 is of an initial strength at Hall effect device 304 based on the distance "Z", the strength of field 338 produced by magnet 308, and the relative orientations of the poles of magnet 308 to Hall effect device 304. As breast 300 engorges with blood during sexual arousal, distance "Z" increases to distance "Z1". Since the relative orientation of magnet 308 to Hall effect device 304 remains relatively unchanged, the change in the signal between unaroused distance "Z" and aroused distance "Z1" is an indicator of the change in distance due to engorgement of the breast with blood during to sexual arousal.

Referring to FIGS. 18 and 19, therein is shown a method for monitoring the respiration rate and depth of breathing using Hall effect device 58 and magnet 62. Hall effect transducer 58 mounted in the region of the sternum 350 of body 256, which acts as a fixed base therefore, by means of an adhesive patch or double-sided adhesive tape 260. Magnet 62 is mounted in the region of the solar plexus 354 of body 256, which moves with respiration, by means of adhesive patch or double-sided adhesive tape 112 with the north pole or south pole typically facing upwardly and the other pole facing downwardly as shown in FIGS. 18 and 19, depending on the particular Hall effect device 68. Magnetic field 114 of magnet 112 produces a signal in wires 68 of Hall effect device 58 based on the angle "C" between magnet 62 and Hall effect device 58. As air is inhaled into the lungs (not shown) angle "C" changes relative to the exhale position such that the signal output in wires 68 changes indicating the frequency and relative depth of breath taken. When used in conjunction with monitoring of swelling and shrinking of the penis or breast, a better indication of arousal is produced with the rate and depth of breathing typically increasing with sexual arousal.

The advantages of the apparatus and methods of the invention over the prior art are numerous. They measure more accurately the swelling and shrinking of the flexible member than prior art devices due to the sensor technology involved and since the device requires little force to operate, unlike devices which must be stretched to operate. They cost significantly less money than prior art devices due to the paper and plastic parts and the low cost of the Hall effect devices and magnets. The first and third embodiment detect penis elongation at the very beginning of sexual arousal, prior to the increase in diameter, which prior art devices do not detect, and produce a greater electrical signal throughout the range thereof. The second and third embodiments detect smaller increases in penis width than prior art devices and produce a greater electrical signal throughout the range thereof. The sensitivity of the apparatus can be changed by using a Hall-effect sensor of a different sensitivity and/or magnets of a different size and/or magnetic field strength. Other advantages include they have no moving parts, they are small & not easily rubbed off of the person's body, they are disposable, and they save labor costs for approximately ten minutes of calibration time per use.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. An apparatus for attachment to an elastic member to sense the swelling and shrinking of the elastic member based on the angularity and displacement of first and second surface portions of the elastic member, comprising:

a first part for movement with the first surface portion;

a second part for movement with the second surface portion, said first and second parts which together create an output signal indicative of the relative angularity and displacement therebetween; and a flexible base having first and second portions, said first part operatively connected to said first base portion and said second part operatively associated with said second base portion, said base having means for attachment to the elastic member such that said first part is juxtaposed the first surface portion for movement therewith and said second part is juxtaposed the second surface portion for movement therewith.

2. An apparatus according to claim 1, wherein the first part is a Hall effect device and the second part is a magnet.

3. An apparatus according to claim 1, wherein the base includes means to initially position the second part relative to the first part, which second part adhesively connects to the second surface portion.

4. An apparatus according to claim 3, wherein:

the elastic member is a woman's breast;

the initial positioning means comprises a notch in the periphery of the second portion of the base to initially engage the second part; and the second part and the base include adhesive portions covered with backing paper which is removed prior to application of the base and the second part to the respective first and second surface portions.

5. An apparatus according to claim 4, wherein the first part is a Hall effect device and the second part is a magnet.

6. An apparatus according to claim 3, wherein:

the elastic member is a man's penis;

the initial positioning means comprises a hole in the periphery of the second portion of the base to initially engage the second part;

the second base portion connects to the penis by means of an elastic band;

the second part includes an adhesive portion covered with backing paper which is removed prior to application of the second part to the second surface portion; and the base includes a perforation between the first and second portions for the second portion to move away from the second part.

7. An apparatus according to claim 6, wherein the first part is a Hall effect device and the second part is a magnet.

8. An apparatus according to claim 1, wherein:

the elastic member is a man's penis;

the second part is connected to the second portion of the base; and the flexible base wraps partially around the penis with the first and second portions juxtaposed first and second surface portions thereof at opposite sides of the penis and is secured by means of an elastic band which engages said first and second base portions.

9. An apparatus according to claim 8, wherein the first part is a Hall effect device and the second part is a magnet.

10. A method of sensing the swelling and shrinking of an elastic member based on the angularity and displacement of first and second surface portions of the elastic member, comprising:

providing an apparatus having first and second sensor parts which create an electrical signal based on the angularity and proximity relative to each other, said first and second parts being operatively connected to first and second portions, respectively, of a flexible base;

attaching the base with sensors to an elastic member; and taking signal readings from the first sensor part.

11. The method of claim 10, wherein:

a third sensor is operatively connected to a third base portion; and as an additional step the sensor third part is connected to a third surface of the penis and disconnected from the third base portion so that said third part can move with the third surface independently of the first and second parts with the respective first and second surfaces of the elastic member.

* * * * *